United States Patent [19]
Wulfman

[11] Patent Number: 6,113,615
[45] Date of Patent: Sep. 5, 2000

[54] ATHERECTOMY BURR INCLUDING A BIAS WIRE

[75] Inventor: Edward Wulfman, Woodinville, Wash.

[73] Assignee: SCIMED Life Systems, Inc., Maple Grove, Minn.

[21] Appl. No.: 09/243,013

[22] Filed: Feb. 3, 1999

[51] Int. Cl.[7] ................................................... A61B 17/22
[52] U.S. Cl. ............................................................ 606/159
[58] Field of Search .................................... 606/159, 170, 606/171, 172, 180

[56] References Cited

U.S. PATENT DOCUMENTS

| | | |
|---|---|---|
| Re. 33,569 | 4/1991 | Gifford, III et al. . |
| 4,669,469 | 6/1987 | Gifford, III et al. . |
| 4,747,405 | 5/1988 | Leckrone . |
| 4,909,781 | 3/1990 | Husted . |
| 4,950,277 | 8/1990 | Farr . |
| 4,979,951 | 12/1990 | Simpson . |
| 5,000,185 | 3/1991 | Yock . |
| 5,071,425 | 12/1991 | Gifford, III et al. . |
| 5,100,424 | 3/1992 | Jang et al. . |
| 5,226,909 | 7/1993 | Evans et al. . |
| 5,242,460 | 9/1993 | Klein et al. . |
| 5,250,059 | 10/1993 | Andreas et al. . |
| 5,269,793 | 12/1993 | Simpson . |
| 5,312,427 | 5/1994 | Shturman . |
| 5,360,432 | 11/1994 | Shturman . |
| 5,370,651 | 12/1994 | Summers . |
| 5,431,673 | 7/1995 | Summers et al. . |
| 5,514,115 | 5/1996 | Frantzen et al. . |
| 5,527,325 | 6/1996 | Conley et al. . |
| 5,569,976 | 10/1996 | Jang et al. . |
| 5,653,696 | 8/1997 | Shiber . |
| 5,836,957 | 11/1998 | Schulz et al. . |
| 5,938,670 | 8/1999 | Keith et al. . |

FOREIGN PATENT DOCUMENTS

| | | |
|---|---|---|
| 0 117519 A1 | 9/1984 | European Pat. Off. . |
| 0 485 133 A1 | 5/1992 | European Pat. Off. . |
| 0 238 217 B1 | 8/1993 | European Pat. Off. . |
| 0 379 786 B1 | 3/1995 | European Pat. Off. . |
| 0 669 106 A2 | 8/1995 | European Pat. Off. . |
| 0 359 447 B1 | 12/1995 | European Pat. Off. . |
| 0 352 872 B1 | 4/1996 | European Pat. Off. . |
| 2057488 | 10/1996 | Russian Federation . |
| 2057489 | 10/1996 | Russian Federation . |
| WO 92/07500 | 5/1992 | WIPO . |
| WO 95/01753 | 1/1995 | WIPO . |
| WO 96/22737 | 8/1996 | WIPO . |
| WO 99/30624 | 6/1999 | WIPO . |

*Primary Examiner*—Michael H. Thaler
*Assistant Examiner*—Vy Q Bui
*Attorney, Agent, or Firm*—Christensen O'Connor Johnson & Kindness PLLC

[57] ABSTRACT

An ablation device (10) includes a drive shaft (12) and an ablation burr (14) secured to the distal end of the drive shaft thereto. A guide wire (18) extends through the drive shaft and the ablation burr. To direct the ablation burr laterally within a patient's vessel, the atherectomy device includes one or more bias wires (30) that extend generally parallel to and spaced from the longitudinal axis of the drive shaft such that engagement of the bias wires against an obstruction in a patient's vessel will force the ablation burr to move laterally within a patient's blood vessel.

To rotate the bias wires in a patient's blood vessel, the bias wire may be coupled to a catheter surrounding the drive shaft. Alternatively, the catheter is designed to engage the bias wires when the drive shaft is retracted into the catheter. The bias wires will then rotate as the catheter is rotated.

8 Claims, 4 Drawing Sheets

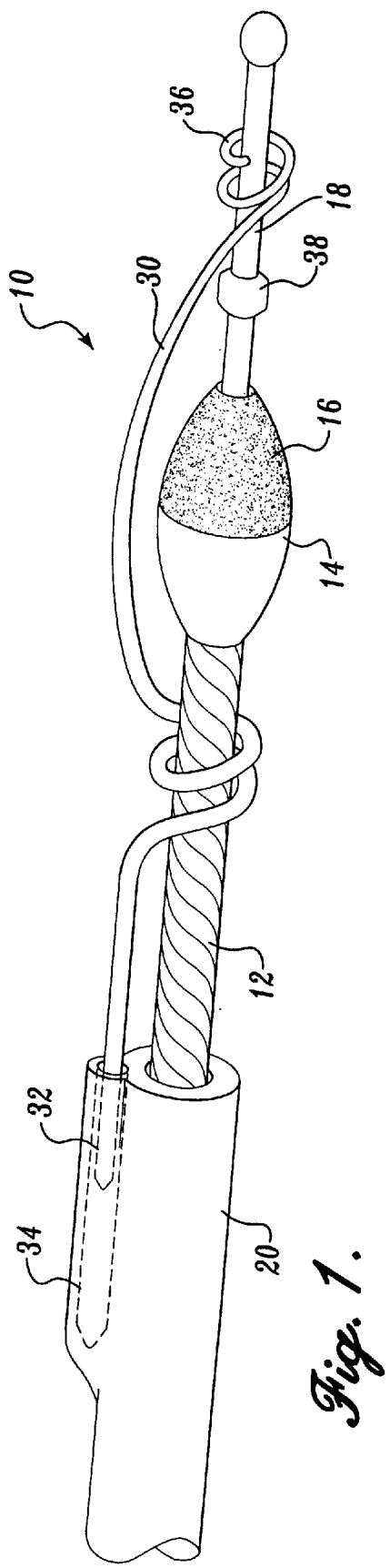
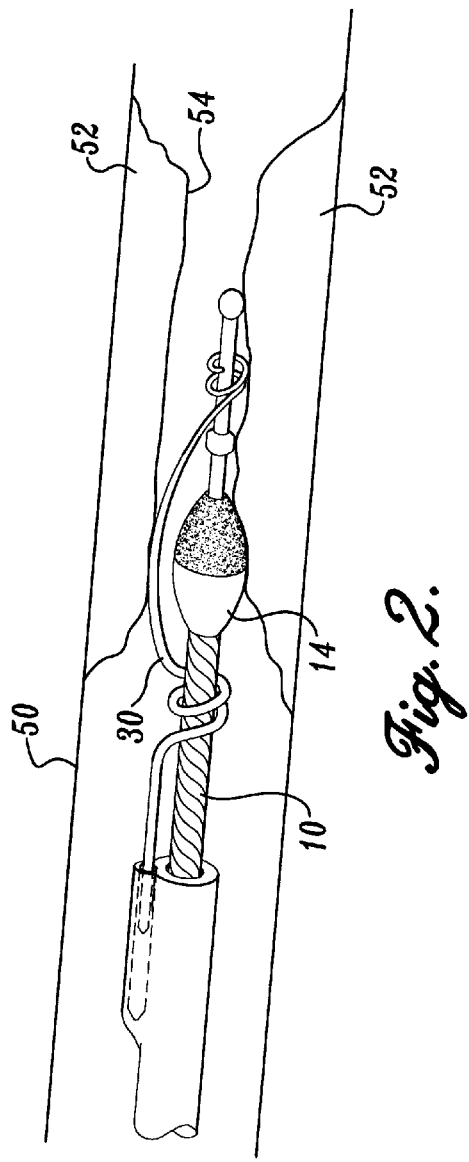

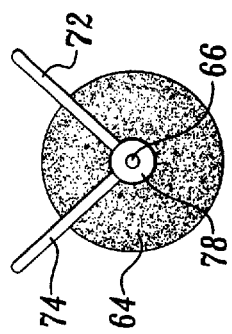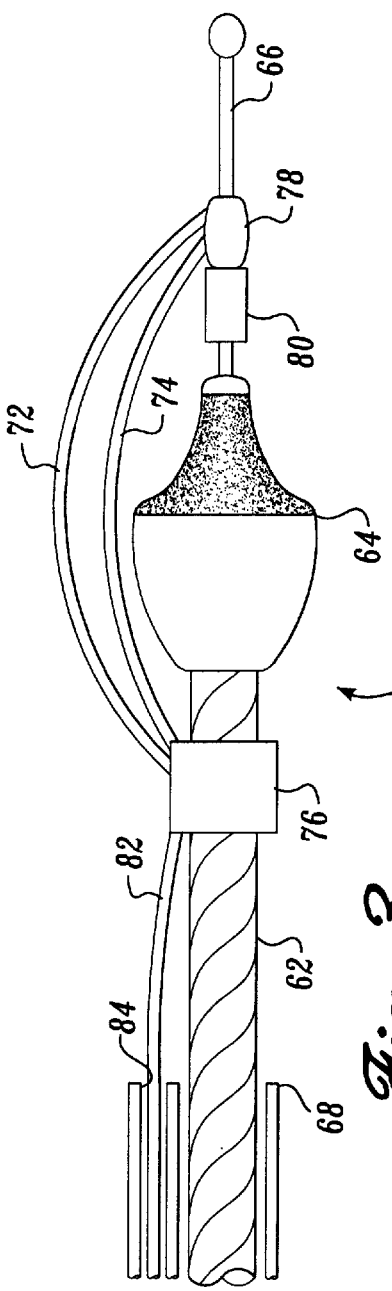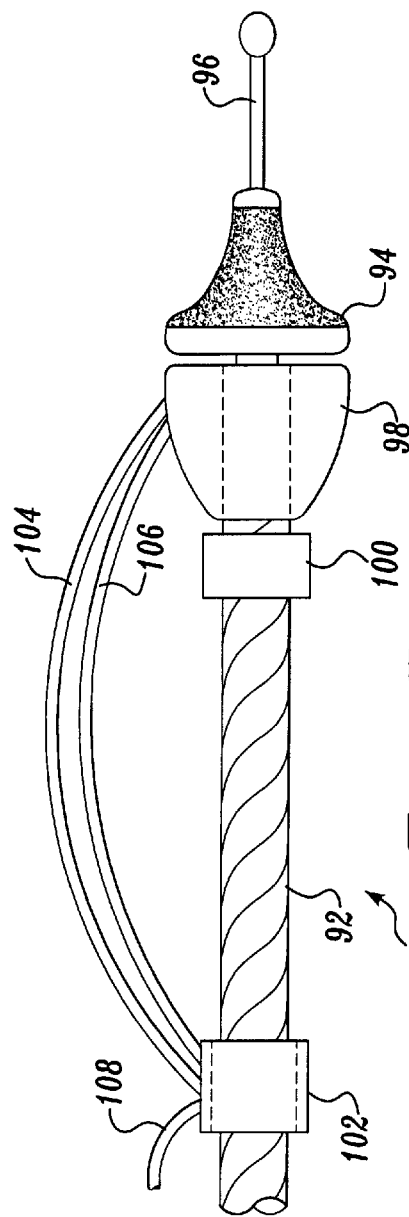

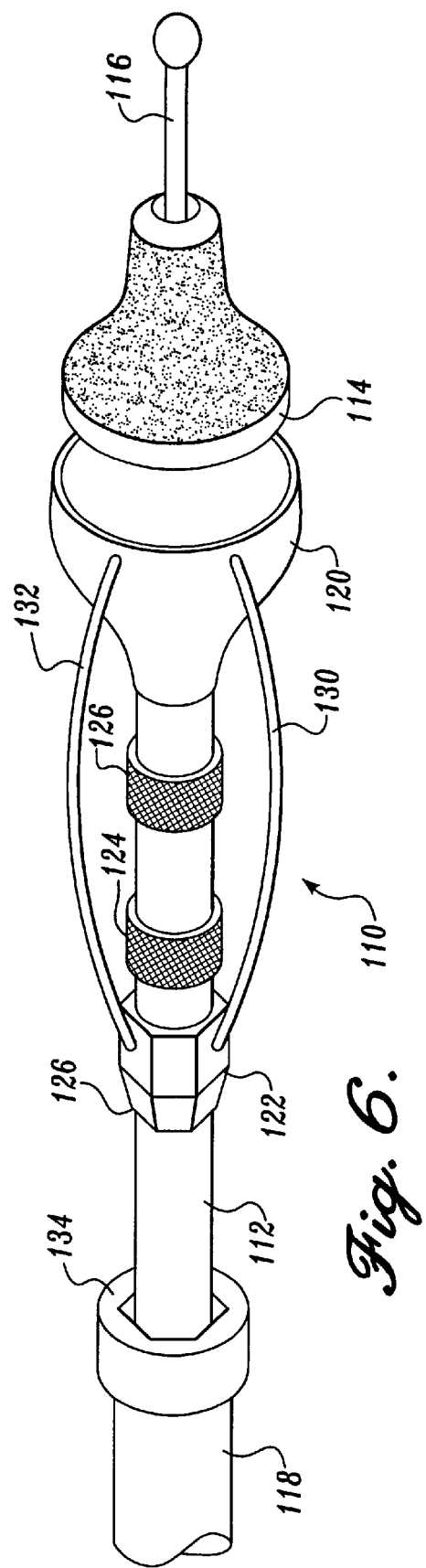

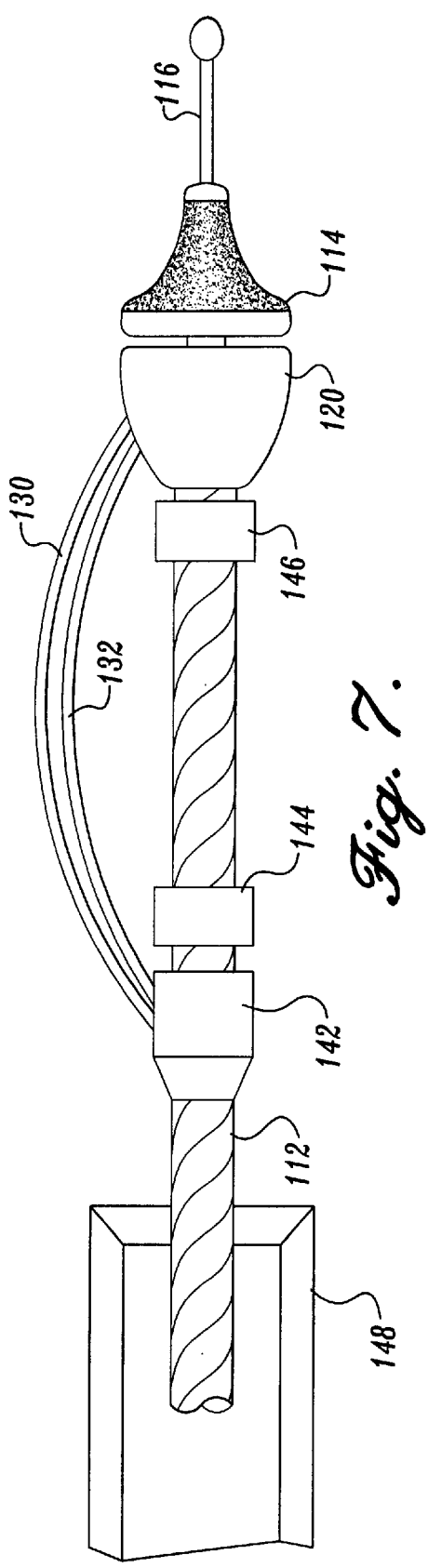
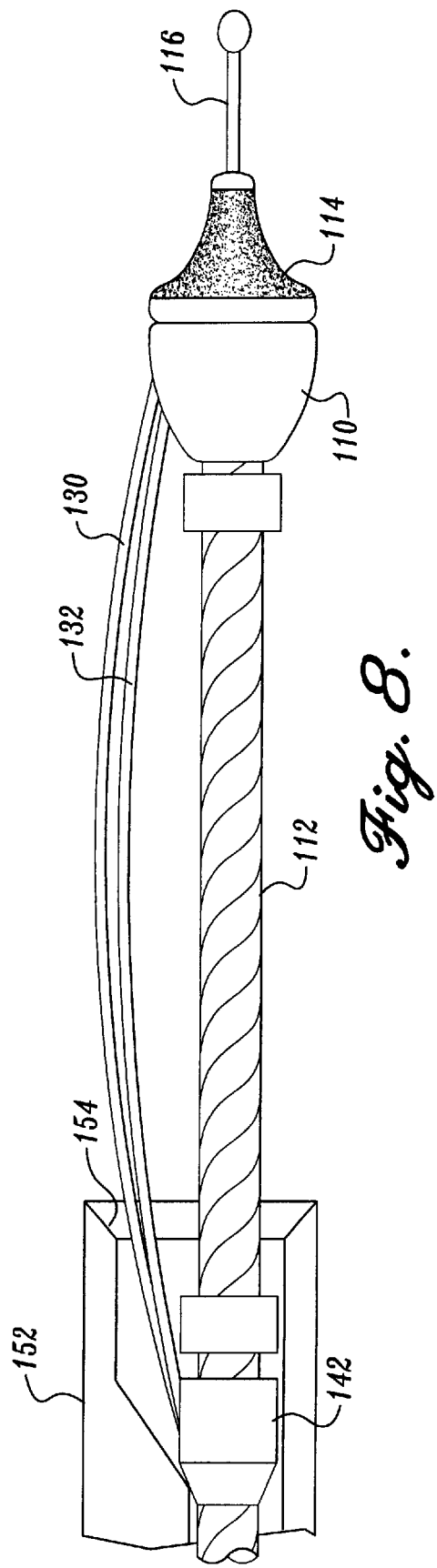

6,113,615

ATHERECTOMY BURR INCLUDING A BIAS WIRE

FIELD OF THE INVENTION

The present invention relates to medical devices in general, and in particular to atherectomy devices that remove deposits from a blood vessel.

BACKGROUND OF THE INVENTION

Vascular disease is one of the leading causes of death in the United States. The most common form of vascular disease is arteriosclerosis in which the blood vessels become partially or totally occluded. Left untreated, such blockages are a major contributing factor to angina, hypertension, heart attacks and strokes.

To treat this disease, many invasive surgical techniques have been developed. For example, cardiac bypass surgery is a commonly performed procedure whereby a blocked cardiac artery is bypassed with a healthy vessel obtained from another location in the patient's body. Because the chest cavity must be opened to perform cardiac bypass surgery, the procedure is not often performed on elderly or relatively frail patients.

To avoid the trauma associated with cardiac bypass surgery, several non-invasive techniques for removing blockages from a vessel have also been developed. One of the most promising is described in U.S. Pat. No. 4,990,134 issued to Auth. With this technique, an incision is made into the patient's femoral artery and a guide wire is advanced through the patient's vasculature to the site of the occlusion. Next, an atherectomy device including a catheter, a drive shaft and an abrasive ablation burr are threaded over the guide wire just proximal to the occlusion. The burr is then rotated by the drive shaft at high speed, typically 100,000–200,000 rpm and advanced over the occlusion. At this high rate of speed, the burr preferentially cuts the harder plaque material in the vessel while leaving the softer vessel tissue uncut.

It has been known for some time that fewer complications occur with the atherectomy procedure when the size of the catheter and the burr are minimized. A small catheter causes less damage at the point where it enters the body. In addition, a smaller catheter and burr can be navigated through smaller blood vessels with less chance of perforation.

While a smaller burr is generally preferable in atherectomy devices for decreasing the likelihood of complications, it limits the size of the lumen that is created in the vessel. Given these constraints, there is a need for an atherectomy device that can minimize the size of the catheter that needs to be introduced into the patient while simultaneously maximizing the size of the lumen that can be ablated in a vessel.

SUMMARY OF THE INVENTION

To increase the size of the lumen that can be created with an ablation burr, the atherectomy device of the present invention includes one or more bias wires that extend generally parallel to and spaced apart from a drive shaft to which the ablation burr is secured. When the bias wires engage an obstruction in a patient's vessel, the ablation burr is displaced laterally in the vessel. The bias wires are then rotated in the vessel and the ablation burr is again passed over the obstruction to increase the size of the lumen.

In accordance with another aspect of the invention, the ablation device may include two or more bias wires that are positioned around the ablation burr to stabilize the burr as it is advanced over the obstruction.

In accordance with yet another aspect of the invention, a catheter surrounding the drive shaft is adapted to engage the bias wires as the drive shaft is retracted into the catheter so that the bias wires can be rotated in the patient's vessel by rotating the catheter.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 illustrates an atherectomy device including a bias wire according to a first embodiment of the present invention;

FIG. 2 illustrates how the bias wire laterally displaces an ablating burr in a patient's vessel;

FIG. 3 illustrates an atherectomy device including a pair of bias wires according to a second embodiment of the present invention;

FIG. 4 illustrates the orientation of the bias wires in the atherectomy device shown in FIG. 3;

FIG. 5 illustrates an atherectomy device having a pair of bias wires that terminate proximally to an ablation burr according to a third embodiment of the present invention;

FIG. 6 illustrates an atherectomy device including a mechanism for rotating a bias wire according to another aspect of the present invention; and FIGS. 7 and 8 illustrate alternative mechanisms for rotating the bias wires in an atherectomy device.

DETAILED DESCRIPTION OF THE PREFERRED EMBODIMENT

The present invention is an atherectomy device having one or more bias wires that cause an ablation burr to directionally ablate an occlusion in a patient's blood vessel.

FIG. 1 illustrates a first embodiment of an atherectomy device that is constructed according to the present invention. The atherectomy device 10 includes a drive shaft 12 having an ablation burr 14 secured to its distal end. The ablation burr 14 is completely or partially coated with an abrasive 16, typically diamond chips or dust, that grinds occluding matter in a patient's blood vessel into pieces that are sufficiently small such that they will not re-embolize downstream. The drive shaft 12 is coupled to a source of rotational motion (not shown) such as an electric motor or turbine that spins the ablation burr at rates between 100,000 and 200,000 rpm.

The drive shaft 12 and ablation burr 14 include a central lumen that allows the drive shaft and burr to be threaded over a guide wire 18. The position of the guide wire 18 can be adjusted by a physician in order to place the ablation burr 14 adjacent an occlusion within a patient's blood vessel. Surrounding the drive shaft 12 behind or proximal the ablation burr is a catheter 20. Typically, the catheter 20 is lined with a low friction material such as Teflon™. The details of the drive shaft 12, ablation burr 14, guide wire 18, and catheter 20 are considered well-known to those of ordinary skill in the art and therefore need not be discussed further except as they relate to the present invention.

As indicated above, in any atherectomy procedure, it is desirable to minimize the size of the catheter and burr that are inserted into the patient. A small catheter and burr reduce the size of the access site made in the patient's femoral artery, are easier to advance through smaller vessels and reduce the chance of vessel perforation. However, a small ablation burr limits the maximum size of the lumen that can be created in the patient's vessel. If the atherectomy device is used in a vessel having a diameter that is significantly larger than the diameter of the burr, then a substantial percentage of an obstruction may not be removed from the vessel and may re-occlude. To solve this problem, the present invention is an ablation device with the ability to directionally ablate an occlusion within a vessel such that a smaller burr can be used to create a larger lumen.

To provide the ability to directionally ablate in a vessel, the present invention is an atherectomy device that includes a bias wire that extends generally parallel to and spaced apart from the longitudinal axis of the drive shaft 12 such that the distance between the bias wire and the outer diameter of the drive shaft 12 is greater than the maximum radius of the ablation burr 14. In the embodiment shown in FIG. 1, the bias wire 30 includes a first end 32 that is slidably inserted into a lumen 34 formed at the distal end of the catheter 20 and adjacent the main lumen through which the drive shaft 12 is passed. The bias wire 30 is looped around the drive shaft 12 at a position proximal to the ablation burr 14 and extends over the ablation burr 14. A second end 36 of the bias wire is looped around the guide wire 18 at a position that is ahead of or distal to the ablation burr 14. If necessary, the atherectomy device 10 may include a bearing 38 made of brass or other suitable material that is positioned between the distal end of the ablation burr 14 and the second end 36 of the bias wire 30. The bearing 38 prevents the abrasive surface 16 of the ablation burr from engaging the bias wire 30 during use.

FIG. 2 illustrates how the bias wire 30 operates to allow the atherectomy device to directionally ablate in a patient's blood vessel. A blood vessel 50 is shown having an obstruction 52 on either side of the vessel wall that may totally or partially occlude the vessel. An initial lumen 54 is cut through the obstruction 52 using an ablation device without the bias wire 30 shown above. The lumen 54 may or may not be centrally located within the blood vessel. Once the initial lumen 54 has been cut, it is generally desirable to increase the size of the lumen in order to decrease the likelihood that the vessel will become re-occluded.

To increase the size of the lumen, the atherectomy device 10 having a bias wire 30 is inserted into the vessel 50 and advanced until the bias wire 30 engages the obstruction 52. As can be seen, when the bias wire 30 engages the obstruction, the bias wire forces the ablation burr 14 to be displaced laterally in the vessel thereby allowing the ablation burr 14 to engage more of the obstruction 52 on the side of the burr opposite the bias wire, thereby increasing the size of the lumen. Because the ablation burr is displaced by the bias wire in one direction, it is typically necessary to rotate the bias wire 30 and pass the ablation burr over the obstruction 52 in order to maximize the size of the lumen created.

In the embodiment shown in FIG. 1, when the ablation burr is retracted towards a distal end of the catheter 20, the first end 32 of the bias wire 30 is retracted into the catheter lumen 34. Therefore, the flex of the bias wire behind or proximal to the ablation burr 14 is reduced and the bias wire 34 can be rotated by rotating the catheter 20.

In some instances, the use of a single bias wire extending over the ablation burr may not be sufficiently strong enough to prevent the ablation burr from slipping into a previously ablated track as the orientation of the bias wire is rotated in the vessel. To counteract this, an ablation device having multiple bias wires may be used. FIG. 3 illustrates an ablation device 60 including a drive shaft 62, an ablation burr 64 disposed at the distal end of the drive shaft, and a guide wire 66 that extends through the center of the drive shaft and ablation burr. The drive shaft 62 is positioned within a central lumen of a catheter 68 in the conventional fashion.

The ablation device 60 includes a pair of bias wires 72, 74 that extend over the ablation burr 64. Each bias wire 72, 74 has a first end that is secured to a slip bearing 76 that is positioned over the drive shaft 62 and proximal to the ablation burr 64 and a second end that is secured to a slip bearing 78 that is positioned over the guide wire 66 and distal to the ablation burr 64. In addition, a bushing 80 may be positioned between the slip bearing 78 and the distal end of the ablation burr 64 to prevent the ablation burr from engaging the bias wires during use.

As shown in FIG. 4, the bias wires 72 and 74 are preferably secured to the slip bearings 76 and 78 at an angle between 20 and 60 degrees with respect to one another such that a triangle is formed between the bias wires 72, 74 and the opposite surface of the ablation burr 64 that is engaging the occluding material in the patient's vessel. With the two bias wires, the ablation burr 64 is held more securely in the patient's vessel and is less likely to slip into a previously ablated track.

It is not necessary that the bias wires extend over the ablation burr in order to displace the burr laterally within the patient's blood vessel. In the embodiment shown in FIG. 5, the atherectomy device 90 includes a drive draft 92, an ablation burr 94 disposed at the distal end of the draft shaft, and a guide wire 96 extending through the draft shaft and the ablation burr. Positioned just proximal to the ablation burr 94 is a slip bearing 98 having a diameter that is a maximum where the slip bearing 98 abuts the ablation burr 94 and tapers towards the drive shaft 92 in the direction proximal to the ablation burr 94. A stop band 100 is secured around the drive shaft 92 just proximal to the slip bearing 98 in order to limit the travel of the slip bearing 98 on the drive shaft 92. A second slip bearing 102 is positioned over the drive shaft 92 proximal to the stop band 100.

A pair of bias wires 104, 106 each have one end secured to the slip bearing 102 and another end secured to the slip bearing 98. The bias wires are gently curved with respect to the drive shaft 92 such that a portion of the guide wire has a radius from the drive shaft that is greater than the maximum radius of the ablation burr 94. As with the embodiment shown in FIG. 4, the bias wires 104, 106 are oriented at an angle between 20 and 60 degrees with respect to each other such that a triangle is formed between the bias wires and the surface of the ablation burr 94 that engages the obstruction in the vessel. To change the orientation of the atherectomy device 90 in the vessel, a wire 108 is secured to the slip bearing 102. The other end of the wire 108 is positioned in a side lumen of a catheter surrounding the drive shaft in the same manner as the embodiments of the invention shown in FIGS. 1 and 3.

As indicated above, the atherectomy device of the present invention will tend to be biased in a direction determined by the orientation of the bias wires in the vessel. In order to ablate the largest possible lumen, it is necessary to re-orient the bias wires and to run the ablation burr over the occluding material. In the example shown in FIGS. 1–5, a wire extends into a side lumen at the distal end of the catheter that surrounds the drive shaft. Therefore, by rotating the catheter with the wire in the side lumen, the bias wires can be re-oriented in the blood vessel and the ablation burr can ablate another path in the obstruction.

FIGS. 6–8 illustrate several different embodiments of the invention whereby the bias wires do not need to be coupled directly to the catheter that surrounds the drive shaft. Turning now to FIG. 6, an atherectomy device 110 includes a drive shaft 112, an ablation burr 114 disposed at the distal end of the drive shaft, and a guide wire 116 that extends through the draft shaft and ablation burr. Surrounding the drive shaft 112 is a conventional catheter 118. As with the embodiment shown in FIG. 5, the atherectomy device includes a slip bearing 120 that is positioned just proximal to the ablation burr 114. A second slip bearing 122 is positioned proximal to the slip bearing 120. To limit the travel of the slip bearings 120 and 122 on the drive shaft 112, a pair of stop rings 124, 126 are secured to the drive shaft between the slip bearings 120 and 122. A pair of bias wires 130, 132 are secured to the slip bearings 120 and 122. The bias wires are oriented at an angle between 20 and 60 degrees with respect to one another in the same manner as the bias wires shown in FIGS. 3 and 4. Again, the bias wires have a maximum radius from the drive shaft that is greater than the maximum radius of the ablation burr.

In order to adjust the position of the bias wires 130, 132 in a patient's blood vessel, the distal end of the catheter 118 is configured to engage the proximal end of the slip bearing 122 such that when the drive shaft is retracted into the catheter, the bias wires can be rotated by rotating the catheter 118.

In the embodiment shown in FIG. 6, the distal end of the catheter 118 includes a cap 134 having a number of vertices into which a correspondingly shaped nut 126 on the proximal end of the slip bearing 122 can be inserted. Preferably, the cap 134 is formed as a six-sided socket that mates with a correspondingly shaped six-sided nut on the slip bearing 122. When an advance knob on the ablation device (not shown) is fully retracted, the nut 126 on the proximal end of the slip bearing 122 engages the cap 134 at the distal end of the catheter such that the bias wires 130 and 132 are held in place and can be rotated by rotating the catheter 118. In operation, a surgeon ablates a path with the bias wires in a particular direction and then retracts the drive shaft until the bias wires are held in place by the cap 134 at the distal end of the catheter. The catheter is then rotated and the ablation burr is advanced to ablate a new path in the patients vessel. This pattern typically continues until the bias wires have been rotated substantially around the circumference of the vessel.

FIGS. 7 and 8 show alternative embodiments for engaging the bias wires in the distal end of the catheter. FIG. 7 illustrates an atherectomy device 140 including a drive shaft 112, an ablation burr 114, a guide wire 116, and a slip bearing 120 that are identical to those components shown in FIG. 6. A pair of bias wires 130, 132 are secured at the one end to the slip bearing 120 and at the other end to a slip bearing 142 that is proximal to the slip bearing 120. To limit the motion of the slip bearings 120 and 142 along the length of the drive shaft, a pair of stop rings 144, 146 are secured to the drive shaft between the slip bearings 120 and 142.

To rotate the bias wires 130, 132, the catheter 148 that surrounds the drive shaft 112 has a lumen with a sufficiently wide opening at its distal end such that a portion of the slip bearing 142 and the bias wires 130, 132 can be drawn into the catheter. Once drawn into the catheter, the slip bearing 142 and bias wires 120, 122 are held in place by a friction fit that allows the bias wires to be rotated in the vessel by rotating the catheter 148. To facilitate the friction fit, the proximal end of the slip bearing 142 may be tapered to cooperate with the size/shape of the lumen within the catheter 148.

An alternative embodiment of the atherectomy device shown in FIG. 7 is shown in FIG. 8. Here, a lumen of a catheter 152 that surrounds the drive wire 112 includes one or more notches 154 disposed at its distal end. The notches are shaped to receive the bias wires 130, 132 as the drive shaft is pulled proximally into the catheter. Once secured in the catheter, the bias wires can be rotated by rotating the catheter. The drive shaft is then moved forward and the bias wires are forced from the notch 154 at the distal end of the catheter and a new path can be ablated.

As can be seen from the above, the present invention is an ablation device that allows a physician to ablate a larger lumen in a patient's vessel without the use of a larger ablation burr. By selectively positioning the one or more bias wires, the ablation burr will be directed laterally in the patient's vessel thereby allowing a larger lumen to be cut in an obstruction.

Although the present invention has been disclosed with respect to its preferred embodiments, those skilled in the art will recognize that changes could be made. Therefore, the scope of the invention is to be determined from the following claims and equivalents thereto.

What is claimed is:

1. An atherectomy device for removing deposits from a vessel, comprising:

a drive shaft;

a catheter through which the drive shaft is routed;

an ablation burr coupled to the drive shaft;

a guide wire extending through the drive shaft and the ablation burr; and a bias wire that displaces the ablation burr in the vessel, wherein the bias wire comprises a first wire having one end slidably affixed in a distal end of the catheter and a second end affixed to a first slip bearing disposed over the drive shaft and proximal to the ablation burr and a pair of wires having a first end secured to the first slip bearing and a second end secured to a second slip bearing disposed over the drive shaft and distal to the ablation burr, the pair of wires forming an angle with respect to each other.

2. The atherectomy device of claim 1, wherein the bias wire extends over the ablation burr and wherein the ablation burr has a concave leading abrasive surface to prevent the abrasive surface from engaging the bias wire.

3. An atherectomy device for removing deposits from a vessel comprising:

a drive shaft;

an ablation burr coupled to the drive shaft;

a guide wire extending through the drive shaft and the ablation burr; and a bias wire extending along a portion of the drive shaft and laterally spaced apart therefrom such that a maximum distance of the bias wire from the drive shaft is greater than a maximum radius of the ablation burr, wherein the engagement of the bias wire against a deposit in the vessel displaces the ablation burr in the vessel; and a first slip bearing positioned over the drive shaft proximal to the ablation burr and a second slip bearing positioned proximal to the first slip bearing, wherein the bias wire is secured to the first and second slip bearings.

4. The atherectomy device of claim 3, further comprising a second bias wire secured to the first and second slip bearings at an angle with respect to the first bias wire.

5. The atherectomy device of claim 4, further comprising a catheter through which the drive shaft is routed, wherein the bias wire further comprises a third wire having a first end secured to the second slip bearing and a second end disposed within a distal end of the catheter.

6. The atherectomy device of claim 3, further comprising a catheter through which the drive shaft is routed, the distal end of the catheter including means for rotating the bias wire.

7. The atherectomy device of claim 6, wherein the means for rotating the bias wire comprises a recess in the distal end of the catheter into which a portion of the bias wire can be retracted to form a friction fit.

8. The atherectomy device of claim 6, wherein the means for rotating the bias wires comprises cooperating locking surfaces on the distal end of the catheter and on a proximal end of the second slip bearing.

* * * * *